United States Patent [19]

Sayers et al.

[11] 4,168,728

[45] Sep. 25, 1979

[54] DISPENSING FLUID INTO INDIVIDUAL CONTAINERS

[75] Inventors: Roger K. Sayers, Rayleigh; Mark A. Samuels, Hullbridge; Harry J. J. Wrenn, Hawkwell; Derek J. Nash, Latchington; Kenneth W. Graham, Buckhurst Hill, all of England

[73] Assignee: Universal Scientific Limited, London, England

[21] Appl. No.: 898,163

[22] Filed: Apr. 20, 1978

[51] Int. Cl.$^2$ .............................................. B67C 3/26
[52] U.S. Cl. ...................................... 141/284; 422/99
[58] Field of Search ............... 141/130, 131, 284, 324; 222/526, 70; 23/253 R, 259

[56] References Cited

U.S. PATENT DOCUMENTS

| | | | |
|---|---|---|---|
| 3,450,173 | 6/1969 | Maizel | 141/130 |
| 3,623,515 | 11/1971 | Gilson | 141/130 |

Primary Examiner—Richard E. Aegerter
Assistant Examiner—Frederick R. Schmidt
Attorney, Agent, or Firm—Larson, Taylor and Hinds

[57] ABSTRACT

Apparatus for use in dispensing fluid into individual containers is disclosed. The apparatus comprises a dispensing head and a transport mechanism comprising an endless conveyor, the dispensing head being attached to the conveyor, which conveyor provides means for moving the dispensing head in a predetermined path above an array of sample containers. A drive arrangement is provided for the transport mechanism, there being a detector incorporated in the drive arrangement for indicating when the drive arrangement has driven the transport mechanism so that the conveyor has moved the dispensing head a predetermined distance along the predetermined path. Furthermore, there is electronic control circuitry for controlling the time during which the head dispenses into an individual container, the circuitry initiating the drive arrangement, to drive the transport mechanism, after repeated time intervals, and being coupled with the detector to stop the drive arrangement in response to an indication from the detector that the drive arrangement has driven the transport mechanism so that the conveyor has moved the dispensing head the said predetermined distance.

8 Claims, 5 Drawing Figures

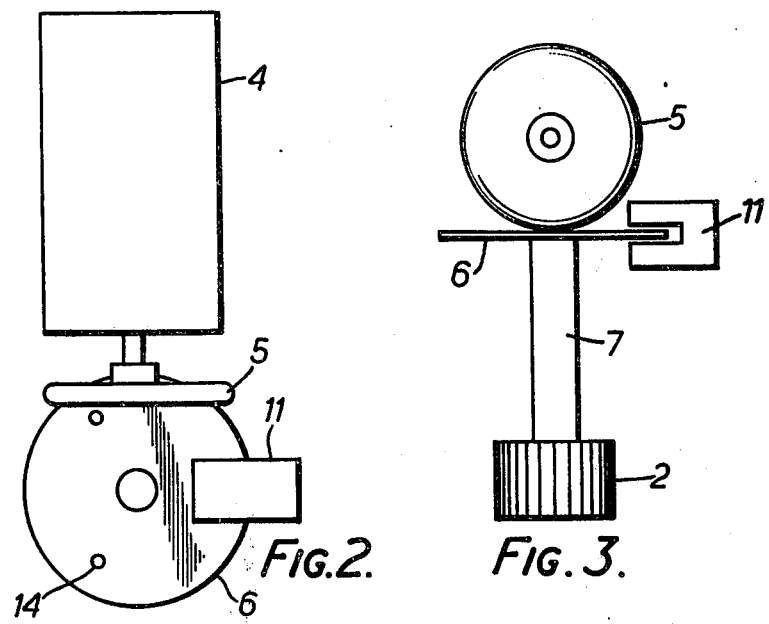
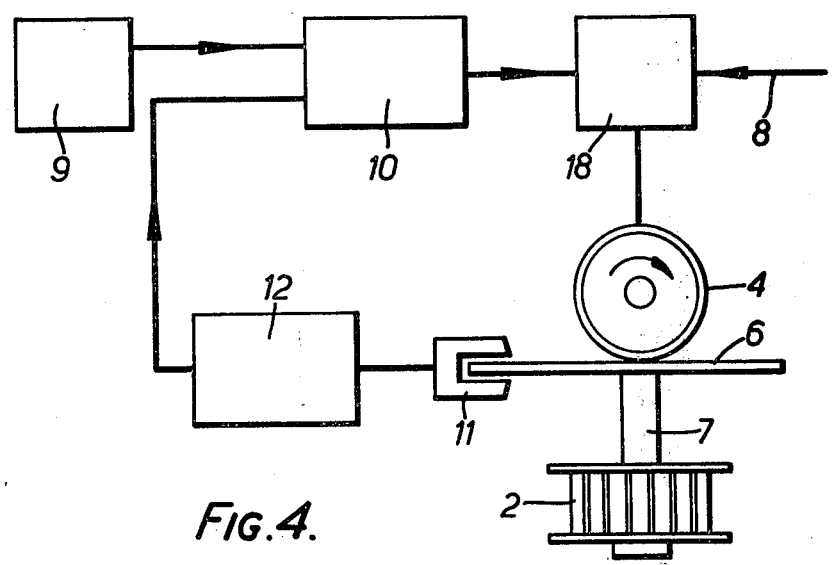

DISPENSING FLUID INTO INDIVIDUAL CONTAINERS

This invention relates to the dispensing of fluid into individual containers.

According to this invention there is provided apparatus for use in dispensing fluid into individual containers, the apparatus comprising:

(a) a dispensing head;

(b) a transport mechanism comprising an endless conveyor, the dispensing head being attached to the conveyor, which conveyor provides means for moving the dispensing head in a predetermined path above an array of sample containers;

(c) a drive arrangement for the transport mechanism;

(d) a detector incorporated in the drive arrangement for indicating when the drive arrangement has driven the transport mechanism so that the conveyor has moved the dispensing head a predetermined distance along the predetermined path; and (e) electronic control circuitry for controlling the time during which the head dispenses into an individual container, the circuitry initiating the drive arrangement, to drive the transport mechanism, after repeated time intervals, and being coupled with the detector to stop the drive arrangement in response to an indication from the detector that the drive arrangement has driven the transport mechanism so that the conveyor has moved the dispensing head the said predetermined distance.

The invention also comprises a combination of such apparatus and a plurality of sample containers above which the dispensing head is moved by the transport mechanism.

The invention will now be described by way of example with reference to the accompanying drawings in which:

FIGS. 2 and 3 are plan and side views of a drive arrangement of the mechanism.

FIG. 4 shows electronic control circuitry in block diagramatic form for controlling the drive arrangement and FIG. 5 is a circuit diagram of an electronic timer circuit of the control circuitry.

Figure 1:
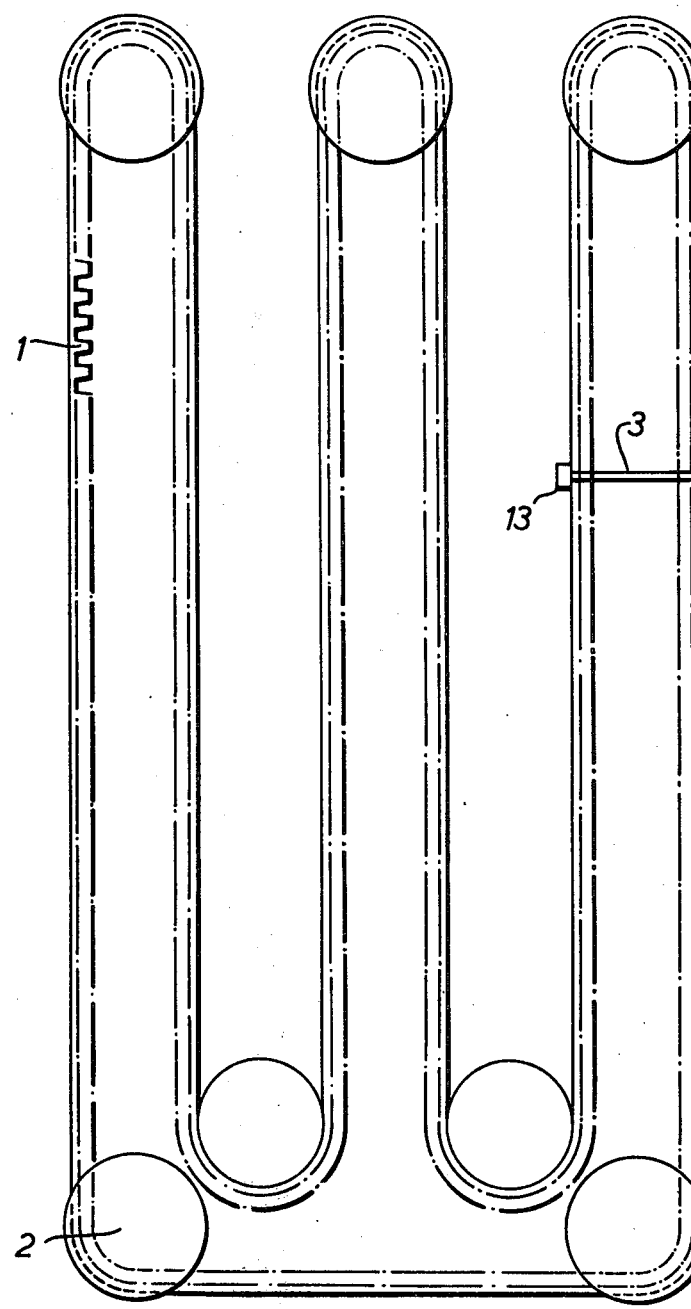
FIG. 1 is an underneath view of part of a transport mechanism for moving a dispensing head.

Referring to FIG. 1, a transport mechanism comprises an endless conveyor in the form of a continuous belt 1 arranged as shown to be driven by rotatable drive gears 2 with which the belt engages, the belt being disposed above a matrix of sample containers in use of the apparatus. The belt 1 could be a toothed belt (as shown) or the endless conveyor could be a chain or some other form of belt allowing drive movement by means of engagement of the belt with rotatable drive pulleys or gears as suitable. A sample input tube 3 and a dispensing head 13 are attached to the belt 1 by a mechanism allowing free rotation in the horizontal plane only. Drive of the transport mechanism is effected by rotating one of the toothed gears 2 by a small electric motor 4, this driving a friction drive disc 5 which drives a disc 6 connected to the toothed gear 2 via a shaft 7—see FIGS. 2 and 3 in the latter of which there is shown a toothed gear 2.

Drive is initiated by applying electrical power from a motor supply line 8 via a motor switch 18 (see FIG. 4 in which there is shown for an alternative example a pulley 2 for a drive belt instead of a gear 2). The switch 18 could be a relay or a solid state device such as a Triac, thyristor or transistor. Control of this switch is derived from a free-running electronic timer circuit 9 which produces a series of pulses which are at regular intervals. The negative edge of each of these pulses sets a bistable circuit 10 to put the motor switch 18 into a conductive state. The motor 4 causes the transport mechanism to be driven until a detector 11 associated with the disc 6 produces an output which, via an amplifier 12, resets the bistable circuit 10 back to its original condition and renders non-conductive the motor switch 18.

The detector 11 is in the example of the opto-interrupter type. The disc 6 has a plurality of accurately spaced holes 14 around its periphery and the detector 11 produces an output signal each time a hole passes through it. Thereby, a pulse occurs which re-sets the bistable circuit 10, rendering non-conductive the motor switch 18. As a result of the action of the detector 11 and the electronic timer circuit 9, the transport mechanism is made to index in accurately repeated increments, the tube 3 remaining stationary over a respective one of a plurality of sample containers in a matrix arrangement each time the motor 4 has been stopped as a result of rendering non-conductive the switch 18 in use of the apparatus. While the tube 3 is stationary, liquid flows from the tube into the container, until the electronic timer circuit 9 sets the bistable circuit 10, thereby rendering conductive the switch 18 to restart the motor 4, the transport mechanism moving the tube 3 until the next hole 14 passes through the detector 11 whereby the motor is stopped with the tube 3 over the next container in the matrix. Thus any liquid which is applied to the sample input tube 3 at a constant rate will be dispensed into separate sample containers in equal volume by virtue of being directed into each container for an equal period of time. The liquid could be flowing continuously through the tube 3, which would be suitable in the case where it drips slowly out of the tube 3.

Figure 5:
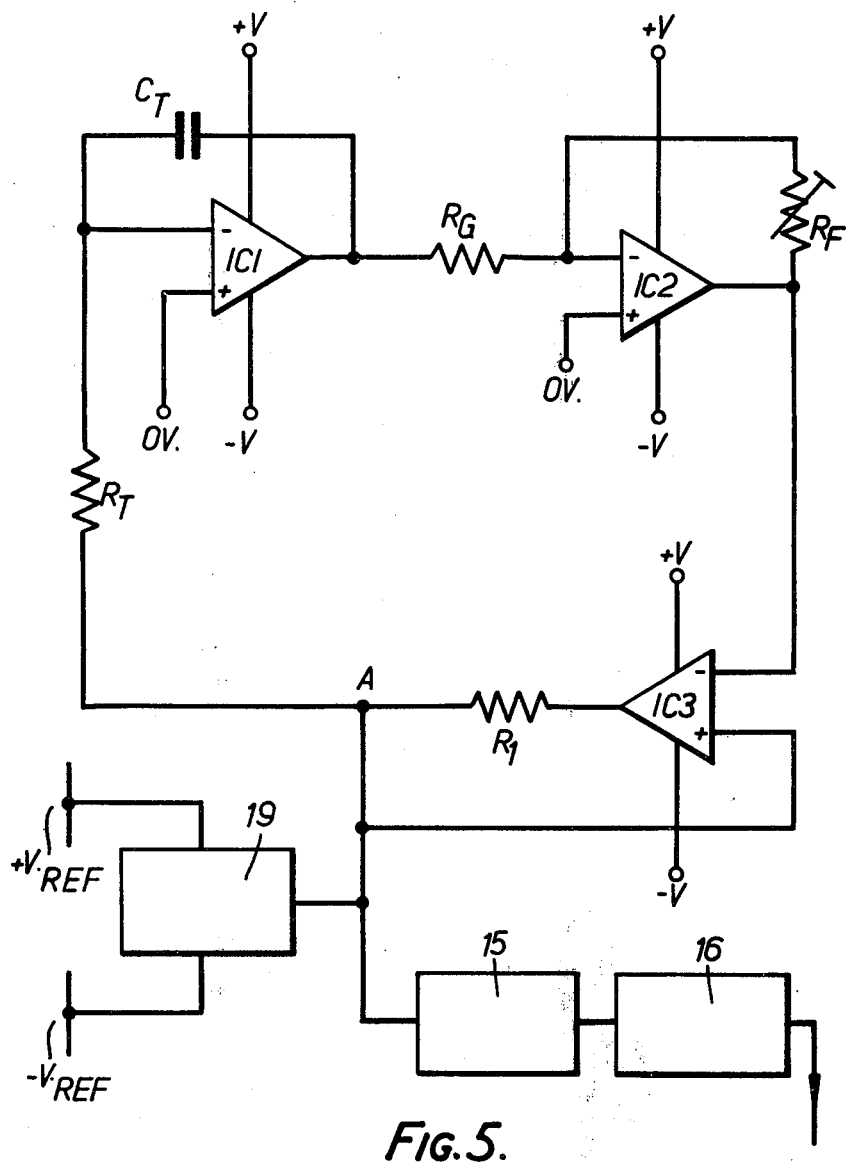

The features of the electronic timer circuit 9 are shown in FIG. 5. IC3 is a conventional operational amplifier connected in a positive feedback mode to give a switching function. For the purposes of description, assume that the output of the amplifier is a positive voltage which is close to the supply voltage +V. A polarity selector 19, which may be an electromechanical or solid state switching device, senses the polarity of this output and connects the point A, to that one of two reference voltages (i.e. +V.REV), of the same polarity.

The point A is then at a voltage +V.REF and a current will flow through a resistor RT and charge a timing capacitor CT. The output voltage of another conventional operational amplifier IC1 will be a negative going ramp, the output of this amplifier being connected via a resistor RG to the inverting input of a further conventional operational amplifier IC2 connected as an inverting amplifier with a gain of RF/RG, i.e. the ratio of the resistance values of the resistor RG and a variable resistor RF. The output voltage of the amplifier IC2 is applied to the inverting input of the amplifier IC3. The output of the amplifier IC3, connected to the point A via a resistor R1, stays at a positive voltage until the voltage applied to its inverting input exceeds +V.REF. Then the voltage at the output of amplifier IC3 switches in a negative direction to a voltage close to the negative supply −V. The polarity selector senses the change in polarity and the point A is connected to the negative reference voltage −V.REF.

The negative going output voltage of the amplifier IC1 changes to become a positive going ramp. The process is repeated with a reversed polarity until the voltage at the point A switches back to +V.REF. Thus, the circuitry described so far operates as a free running oscillator producing a pulse at point A of magnitude 2V.REF with a repetition rate set by the time constant CT.RT of the resistor RT and the capacitor CT and the gain RF/RG of the amplifier IC2. For convenience, the values of CT and RT are fixed and the period of the oscillator determined by the values of RG and RF, the latter being variable. This allows resistor RF to be located remote from the rest of the circuitry. The pulses obtained at point A are applied to a pulse shaping circuit 15 and then to a binary divider circuit 16 to lengthen the period.

We claim:

1. Apparatus for use in dispensing fluid into individual containers, the apparatus comprising:
  (a) a dispensing head;
  (b) a transport mechanism comprising an endless conveyor, the dispensing head being attached to the conveyor, which conveyor provides means for moving the dispensing head in a predetermined path above an array of sample containers and is above the sample containers in use of the apparatus;
  (c) a drive arrangement for the transport mechanism, the drive arrangement comprising a motor provided with a disc which rotates as the motor drives the transport mechanism;
  (d) a detector incorporated in the drive arrangement for indicating when the disc has rotated by an amount such that the motor has driven the transport mechanism so that the conveyor has moved the dispensing head a predetermined distance along the predetermined path; and
  (e) electronic control circuitry for controlling the time during which the head dispenses into an individual container, the circuitry initiating the motor to drive the transport mechanism, after repeated time intervals, and being coupled with the detector to stop the motor in response to an indication from the detector that the motor has driven the transport mechanism so that the conveyor has moved the dispensing head the said predetermined distance, the control circuitry comprising:
  (i) timer circuitry for producing a pulse train; and
  (ii) trigger circuitry coupled between the timer circuitry and the motor, the trigger circuitry being set from a first state to a second state after said repeated time intervals to initiate the motor to drive the transport mechanism and the trigger circuitry being coupled with the detector to be set from said second state to said first state to stop the motor in response to an indication from the detector that the motor has driven the transport mechanism so that the conveyor has moved the dispensing head the said predetermined distance.

2. Apparatus according to claim 1, wherein the detector comprises means for detecting by means of optical interruptions when the disc has rotated by an amount such that the motor has driven the transport mechanisms so that the conveyor has moved the dispensing head to the said predetermined distance.

3. Apparatus according to claim 1 which is such that the transport mechanism provides means for moving the dispensing head in a predetermined path above a matrix of sample containers.

4. Apparatus according to claim 1, wherein the dispensing head is provided with a sample input via which it dispenses fluid into a given container.

5. Apparatus according to claim 4, wherein the sample input is in the form of a tube.

6. Apparatus according to claim 1, wherein the conveyor is an endless belt.

7. Apparatus according to claim 6, wherein the belt is a toothed belt.

8. Apparatus according to claim 1, in combination with a plurality of sample containers above which the dispensing head is moved by the transport mechanism.

* * * * *